United States Patent [19]

Tankersley

[11] 4,251,510

[45] Feb. 17, 1981

[54] INTRAVENOUSLY INJECTABLE SOLUTION OF PLASMA PROTEIN FRACTION FREE FROM BRADYKININ, KININOGEN AND PREKALLIKREIN ACTIVATORS AND PROCESSES FOR ITS PRODUCTION

[75] Inventor: Donald L. Tankersley, Rockville, Md.

[73] Assignee: Cutter Laboratories, Inc., Berkeley, Calif.

[21] Appl. No.: 66,757

[22] Filed: Aug. 15, 1979

Related U.S. Application Data

[63] Continuation-in-part of Ser. No. 928,943, Jul. 28, 1978, which is a continuation-in-part of Ser. No. 800,503, May 25, 1977, abandoned.

[51] Int. Cl.³ .................... A61K 35/14; A61K 37/00; C07G 7/00
[52] U.S. Cl. .................... 424/101; 424/177; 260/112 B
[58] Field of Search .................... 260/112 B; 424/101, 424/177

[56] References Cited

U.S. PATENT DOCUMENTS

| | | | |
|---|---|---|---|
| 2,958,628 | 11/1960 | Hink | 260/112 B |
| 3,100,737 | 8/1963 | Auerswold et al. | 424/101 |
| 3,686,395 | 8/1972 | Stephan | 424/101 |
| 3,876,775 | 4/1975 | Izaka et al. | 424/177 |
| 4,000,121 | 12/1976 | Garcia | 260/112 B |
| 4,017,470 | 4/1977 | Izaka et al. | 260/112 B |

OTHER PUBLICATIONS

Margolis, Thromb. Diath. Haemor., Suppl. 4, 132–136 (1959).

Soulur, Thromb. Diath. Haemor., Suppl. 4, 137–141 (1959).

*Primary Examiner*—Delbert R. Phillips
*Attorney, Agent, or Firm*—Robert E. Allen; Theodore J. Leitereg

[57] ABSTRACT

Plasma Protein Fraction substantially free of bradykinin, kininogen and prekallikrein activators is obtained by treating Cohn Supernatant II plus III at about neutrality with a siliceous substance for a period of time sufficient to bring about essentially complete conversion of intrinsic kininogen into bradykinin. Subsequently, after being separated from Cohn Fraction IV-1, the Plasma Protein Fraction is reconstituted and held for a period of time sufficient to allow substantially complete destruction of bradykinin by kininase. Methods are disclosed for the destruction of prekallikrein activators which may be present in Plasma Protein Fraction.

3 Claims, No Drawings

INTRAVENOUSLY INJECTABLE SOLUTION OF PLASMA PROTEIN FRACTION FREE FROM BRADYKININ, KININOGEN AND PREKALLIKREIN ACTIVATORS AND PROCESSES FOR ITS PRODUCTION

This is a continuation-in-part of application Ser. No. 928,943, filed July 28, 1978, which application is a continuation-in-part of application Ser. No. 800,503, filed May 25, 1977, now abandoned.

BACKGROUND OF THE INVENTION

This invention relates to Plasma Protein Fraction (Human) substantially free of bradykinin, kininogen, and activators of prekallikrein, and to methods for producing same.

For a number of years, solutions of Plasma Protein Fraction (Human) have enjoyed extensive use in the treatment of shock, hypoproteinemia and other conditions requiring the use of plasma expanders. Plasma Protein Fraction (Human) is the official nomenclature which has been adopted in the U.S. by the FDA (21 CFR 640.90) for the product as obtained by the modified Cohn fractionation process applied to human plasma as disclosed in U.S. Pat. No. 2,958,628. Plasma Protein Fraction (Human) also called PPF (Human), is a mixture of constituent plasma proteins and under 21 CFR 640.90 shall consist of at least 83% albumin and no more than 17% globulins of which no more than 1% shall be gamma globulin. The globulins are a mixture of α- and β-globulins, and actually only those species of α- and β-globulins having molecular weights similar to that of albumin (see U.S. Pat. No. 2,958,628). The constituent plasma proteins in Plasma Protein Fraction (Human) therefore make up a substantially unique mixture which differs from other plasma fractionation products obtained by different processes even though these other products may include albumin and α- and β-globulins.

Vasodepressor effects have sometimes been noted when PPF solutions were infused rapidly or used in cardiopulmonary bypass procedures, a condition which could by extremely hazardous to a patient. The presence of bradykinin in such solutions was implicated according to Izaka et al (Transfusion 14, pp. 242–248, 1974) and methods for removing bradykinin from PPF by physical means were disclosed in U.S. Pat. No. 3,876,775. Such means included exposing the PPF solutions to silica gel or cation exchange resins to adsorb the bradykinin. These methods have the disadvantage of also adsorbing some of the desired plasma proteins and thereby reducing the yield of PPF.

It has been observed in our laboratories that certain lots of PPF solution which were shown to be substantially free of bradykinin, nevertheless caused a depressor effect when infused rapidly into dogs. Investigation of such solutions revealed that they had significant amounts of kininogen present. It was postulated that this precursor was converted into bradykinin by the action of kallikrein or other proteases circulating in the dog's blood stream. Patients in shock, particularly those in which shock is brought about by endotoxins or pancreatitis, could be seriously compromised if Plasma Protein Fraction containing kininogen were rapidly infused since their blood pressure is already greatly depressed.

In U.S. Pat. No. 4,017,470, Izaka et al, there is described a method for the production of a heat-stable plasma protein fraction and it is stated the product has no blood pressure depressing action. The product is disclosed as containing 93–95 percent albumin and 5–7 percent of alpha globulin. The product is derived from Cohn's Fraction IV-1 by a process which includes (1) heating a solution of Fraction IV-1 at pH 4.5 to 5.5 at 50°–65° C. with an organic acid for 1 to 4 hours to precipitate most of the unstable lipo- and glycoproteins; (2) treating the supernatant with Rivanol ® to precipitate the residual lipoprotein, and (3) adsorbing peptide substances showing blood pressure-depressing action (by rat uterus contraction test) which are formed from blood pressure-depressing substances such as kininogen with an inorganic adsorbent (e.g., silica gel or cation exchanger). This third step is, of course, the same as that disclosed in U.S. Pat. No. 3,876,775 (supra), which describes the removal of bradykinin from Plasma Protein Fraction. To avoid any confusion from statements in the U.S. Pat. No. 4,017,470 which refer to "blood pressure-depressing substances such as kininogen", it is well known that kininogen itself exhibits no depressor effect in the rat uterus test; hence, Izaka et al obviously intended such statements to mean kininogen has the potential for producing depressor substances. In any event, there is no indication that their product is free of kininogen. Moreover, their product is not Plasma Protein Fraction but quite a different mixture whose constituent plasma proteins differ significantly from those of PPF.

Recently, it was noted in our laboratories that occasional production lots of PPF resulted in solutions which caused a depressor effect when rapidly infused into patients. These particular lots were demonstrated to be essentially free of bradykinin, and kininogen was at levels which were considered to contribute little if any toward this depressor action. Further investigation of these solutions showed the presence of significant amounts of activator(s) of prekallikrein (PKA). It was postulated that the PKA in these solutions when injected would then activate the endogenous prekallikrein and lead to the formation of bradykinin in the blood stream.

The sequence of events which is generally postulated for the generation of bradykinin is expressed by the following:

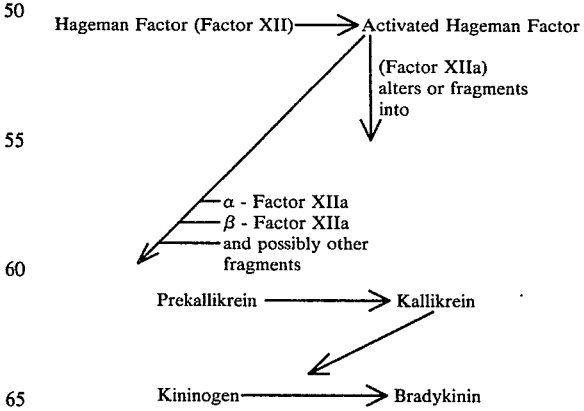

In the Cohn method of fractionating plasma, or modifications thereof, some Factor XIIa is most likely generated, some of which may become altered or fragmented. It is believed these altered or fragmented species, as well as intact activated Hageman Factor (Factor XIIa), cause the conversion of prekallikrein to kallikrein. Varying amounts of kininogen, depending on slight changes in the process, are converted by the action of kallikrein into the potent hypotensive substance, bradykinin.

It would be an important improvement if solutions of Plasma Protein Fraction could be consistently prepared which were substantially free not only of bradykinin but also of activators of prekallikrein and kininogen. Quite recently the problem was similarly expressed by Culliver et al (Vox. Sang. 36, pp. 201–207, 1979), although no solution to the problem was offered.

Auerswald et al disclose in U.S. Pat. No. 3,100,737 a heat stable plasma fraction consisting of albumin and alpha and beta globulins derived from plasma by a process similar to the process of the U.S. Pat. No. 4,017,470 but quite different from the modified Cohn fractionation process of the U.S. Pat. No. 2,958,628. Following the removal of fibrinogen and gamma globulin by ammonium sulfate precipitation, the supernatant is mixed with fatty acids and heated at 55° C. for 20 minutes at pH 5.2 to precipitate unstable alpha and beta globulins. In one example, the ammonium sulfate is removed by passing the second supernatant over cationic and anionic resin exchangers which conceivably might also remove any bradykinin present in the final product. Apart from the belief that their product would have constituent plasma proteins differing from those in PPF since the relative processes are so different, there is no indication that their product would be substantially free of either kininogen or activators of prekallikrein.

SUMMARY OF THE INVENTION

The present invention discloses Plasma Protein Fraction (Human) and solutions thereof substantially free of bradykinin, kininogen, and activators of prekallikrein, and to processes for obtaining same.

Plasma Protein Fraction (PPF) whenever stated in the disclosure and claims is herein defined as that mixture of heat stable plasma proteins obtained by the modification of the Cohn fractionation process as disclosed by Hink in U.S. Pat. No. 2,958,628 and which meets the specifications for composition as expressed in sections 640.91 and 640.92 to Title 21 Code of Federal Regulations, incorporated herein by reference.

Activators of prekallikrein are intended to include activated Hageman Factor (Factor XIIa) and any altered form or fragment of active Hageman Factor capable of activating prekallikrein, as for example, those currently designated as $\alpha$-XIIa and $\beta$-XIIa.

Activation of Factor XII can be brought about by contacting blood plasma with a number of substances such as glass, Celite ® (diatomaceous earth), aluminum silicate, and certain forms of alumina to name a few (J. Margolis, Thromb. Diath. Haemor, Suppl. 4, pp. 132–136, 1959; J. P. Soulier, Ibid. pp. 137–141; J. Margolis, Ann. N.Y. Acad. Sci. 104, pp. 133–145, 1963).

It has also been shown that normal blood plasma contains a heat labile proteolytic enzyme or kininase, a carboxypeptidase, which acts on bradykinin to degrade bradykinin so that its hypotensive effect is obliterated (S. Morichi and K. Izaka, Transfusion 16, pp. 178–181, 1976; V. A. Bokisch and H. J. Mueller-Eberhard, J. Clin, Invest. 49, pp. 2427–2436, 1970).

I have discovered that certain modifications in the Hink process will assure the production of PPF which is substantially free of bradykinin, kininogen, and activators of prekallikrein, these modifications being of a nature which does not alter the inherent composition of PPF.

I have found that, at a stage following the removal of Fraction II+III in the Hink process, if a solution of the remaining plasma proteins at or about neutrality is treated with a siliceous substance in amounts sufficient to activate Hageman Factor present in the solution, and held for a sufficient period of time, that substantially all kininogen present will be converted to bradykinin.

It is important that the kininogen be essentially completely depleted at this point to insure against its conversion to bradykinin during later processing of the PPF where any generated bradykinin would not be removed by separation procedures or destroyed by kininase. The kininogen-free material is then held at about neutrality for a period of time essential for the destruction by carboxypeptidase of substantially all the bradykinin present. The material thus obtained will be substantially free of bradykinin and kininogen. The period of time necessary for the destruction of essentially all of the bradykinin by carboxypeptidase has been found to be quite short, i.e., only a few hours. I have also found that if solutions of such fractions are held for longer periods of time, substantially all of any prekallikrein activators which are present will be destroyed. Solutions of heat stable Plasma Protein Fraction can then be heated at 60° C. for at least 10 hours to assure destruction of any hepatitis virus which may be present. Alternatively, solutions containing Plasma Protein Fraction can be treated with the siliceous material, held for the shorter period of time required for destruction of bradykinin, then heat pasteurized, and finally further heated at elevated temperatures either at neutrality or at higher or lower pH for a time sufficient to destroy all or substantially all of any prekallikrein activators present. Modifications of these processes are also possible and will be disclosed in detail. The preferred starting point in the process for obtaining PPF substantially free of bradykinin, kininogen, and activators of prekallikrein is Supernatant II+III in the Hink process.

The siliceous substance found most effective for activation of Hageman Factor can be a number of different materials, as for example, glass or diatomaceous earth. Preferred are the diatomaceous earths, for example, such as those commercially available by the name Celite ® filter aids, the most preferred grade being Super-Cel ® filter aid (JohnsManville Corp.). The term siliceous substance is intended to mean silicon dioxide in its various forms and does not include other compounds of silicon such as silica gel which is a precipitated silicic acid and which is ineffectual in the activation of Hageman Factor.

Cohn Supernatant II plus III contains about 3 percent protein and the amount of siliceous substance necessary for activation of Hageman Factor can vary but generally should be in the range of about 0.1 to 5.0 grams per liter of Supernatant II plus III, preferably about 1 g. per liter when one of the diatomaceous earths is used. The pH of the solution can vary between about 6.0 and 8.0 but preferably about 6.8 to 7.4. Although activation of the various components in the kinin generation system occurs rapidly in a few minutes at higher temperatures, i.e., at around ambient to about 38° C., activation will also take place, albeit more slowly, at lower temperatures, i.e., at −7° to about +5° C. At these lower temperatures, the solution should be in contact with the siliceous material for at least 5 to 20 hours, preferably about 14 hours to be assured essentially all kininogen present has been converted to bradykinin. Fragments or altered forms of activated Factor XII are presumably formed at this stage, $\beta$-XIIa probably predominating.

Following treatment with the siliceous material, the mixture may first be filtered or centrifuged to remove the siliceous material and the clear solution then adjusted to a pH value of about 5.3 to cause Cohn Fraction IV-1 to precipitate. Alternatively, the pH of the mixture may first be adjusted and Fraction IV-1 precipitated, whereupon the siliceous material is removed with Fraction IV-1 by filtration or other means.

The PPF can be isolated by the method described in U.S. Pat. No. 2,958,628; namely by bringing the ethanol content of the Supernatant IV-1 to about 30 percent and lowering the pH to about 4.6. The precipitated PPF is collected as a wet paste and lyophilized or the paste may first be washed with acetone to remove most of the water and air dried. Although much of the bradykinin present in Supernatant IV-1 is physically removed by remaining in the discarded supernatant after separation of the wet paste, significant amounts still adhere to the precipitated fraction.

The dried Plasma Protein Fraction is then reconstituted with water, preferably to about a 5 percent solution to which stabilizers may be added, such as sodium acetyltryptophan and sodium caprylate. In addition, pharmaceutically acceptable salts such as sodium chloride and sodium acetate may be added. In the Hink process, solutions of heat-stable Plasma Protein Fraction were promptly heated at 60° C. for at least 10 hours (to destroy any hepatitis virus which may be present). However, in order to be certain that substantially all bradykinin present is degraded, the bulk solution of PPF is first allowed to stand for a period of time which will permit the heat-labile carboxypeptidase present in the solution to bring about this degradation.

At ambient temperatures the degradation of bradykinin is quite rapid. At lower temperatures, i.e., at around 5° C., the bulk solution should be held for several hours, or until an aliquot has been shown to contain essentially no bradykinin by standard test procedures. Generally this hold period at about 5° C. is about 24 hours.

Other modifications for the elimination of bradykinin are possible. For example, the wet paste obtained by precipitation of the protein from Supernatant IV-1, after reconstitution to a desired concentration, can be diafiltered to remove ethanol and other unwanted low molecular weight substances. During the diafiltration, bradykinin is removed not only physically but also by the degrading effect of carboxypeptidase. Alternatively, the protein in Supernatant IV-1 need not be isolated by precipitation and subsequently held as a 5 percent reconstituted solution as described hereinbefore. After first adjusting the pH of Supernatant IV-1 to about neutrality, this solution may be ultrafiltered through an appropriate membrane, as for example, through an SM-10 membrane (available from the Amicon Corporation, Lexington, Mass.), or its equivalent, until the desired protein concentration is obtained. Diafiltration may follow until essentially all the ethanol and/or any other unwanted low molecular weight substances are removed. Some or most of the bradykinin present will also be physically removed and the degrading action of carboxypeptidase on any residual bradykinin will have transpired during this procedure.

If complete or substantially complete destruction of prekallikrein activators (PKA) is desired at a hold stage of the process, this can be accomplished by holding the solution for longer periods of time. Generally, at ambient temperatures, approximately 24 hours hold time is required. At about 5° C., destruction of PKA is not quite complete in 24 hours so that a hold period somewhat longer than 24 hours is necessary. Alternatively, after a hold period of about 24 hours at around 5° C., the solution may be heated at about 60° C. for at least 10 hours at neutrality or for shorter periods of time at lower or higher pH, e.g., about 5.5 or about 8.2. With any of these alternatives, the solution of the heat stable Plasma Protein Fraction should be adjusted to neutrality if necessary and heated at least 10 hours at 60° C. to assure destruction of any hepatitis virus which may be present.

Another alternative method for obtaining PPF of this invention involves heating the neutral solution at 60° C. for 10 hours (to destroy hepatitis virus) immediately after the shorter hold period which destroys substantially all the bradykinin present but which is insufficient to destroy all the PKA present. The pasteurized solution can then be heated at about neutrality at around 60° C. for a period of time sufficient to reduce the amount of PKA to at least levels which would cause only an insignificant depressor effect when the solutions of Plasma Protein Fraction are injected. This period of time can be materially shortened if slightly higher temperatures than 60° C. are used, e.g. about 65° C., or if the pH of the solution is lowered, e.g., to about 5.5.

In any of the above procedures, if temperatures above 5° C. are employed at any stage or where ethanol is not present in the solutions, it is preferable to sterile filter these solutions prior to the hold periods to prevent bacterial growth which would be favored by the higher temperatures if bacteria were present in the initial plasma. In addition, in any of the above described processes, optionally one can heat the neutral solutions of the PPF at about 60° C. for about two hours (just prior to the hepatitis destroying pasteurization step) and sterile filter into final containers. This optional step will allow for the removal of trace contaminating proteins which occasionally precipitate in heat treatment.

Solutions of Plasma Protein Fraction obtained by the processes of this invention can be rapidly infused intravenously with little or no decrease in blood pressure resulting from such infusion since the solutions contain substantially no kininogen, activators of prekallikrein, or bradykinin. The safety of such a product would be particularly evident when used as a primer for heart-lung machines used in open heart surgery and in the treatment of shock when large volumes are often administered.

It is believed that one skilled in the art can, using the preceding description, utilize the present invention to its fullest extent. The following preferred specific embodiments are therefore to be construed as merely illustrative, and not limitative of the remainder of the disclosure in any way whatsoever.

DETAILED DESCRIPTION OF PREFERRED EMBODIMENTS

Starting Material

The preferred starting point for experimental studies was Cohn Supernatant II plus III obtained by the process described in U.S. Pat. No. 2,958,628, incorporated herein by reference. This Supernatant contains approximately 3 percent of a mixture of plasma proteins consisting chiefly of albumin, globulins and lipoproteins.

Test for Bradykinin

Smooth muscle contractibility as a measure of the amount of bradykinin present in a sample was determined by the method of Magnus, details of which are described in U.S. Pat. No. 3,876,775, incorporated herein by reference. Synthetic bradykinin, obtainable from Beckman Instruments, Inc., Bio-products Dept., Palo Alto, California, was used as the standard.

Test for Kininogen

The method used was adapted from the method of Donaldson et al (J. Lab. Clin. Med. 87, pp. 327–337, 1976) which involves converting kininogen to bradykinin. Test samples (1 to 10 ml.) are heated for 2 hours at 60° C., cooled to room temperature and incubated with trypsin (50 µg./ml.) for 2 hours. Following incubation, soybean trypsin inhibitor (0.25 mg./ml.) is added and the amount of bradykinin is determined by the method described supra. The amount of kininogen present in a sample is expressed as nanograms of bradykinin equivalents.

Assay for Prekallikrein Activator (PKA) in Heat Stable Plasma Protein Fraction (PPF)

The prekallikrein (PK) used in this assay is isolated from human plasma by the method of K. Laake and A. M. Venneröd, Thrombosis Research, 2, pp. 393–407 (1973), except that the PK from the initial DEAE-Sephadex chromatography step is suitable for use in this assay without further purification. The prekallkrein thus obtained is stored frozen at a concentration of one unit per milliliter in phosphate-buffered-saline at a pH of 7.5. Phosphate-buffered-saline (PBS) is prepared by dissolving 8.77 grams (0.15 mole) of sodium chloride and 6.90 grams (0.05 mole) of sodium dihydrogen phosphate monohydrate in about 800 milliliters of water, adjusting to either pH 7.5 (for PBS pH 7.5) or pH 8.0 (for PBS pH 8.0) using about 4 percent sodium hydroxide solution and diluting to a final volume of one liter.

For the purpose of this assay, one unit of PK is defined as that amount which generates one unit of kallikrein upon complete activation. One unit of kallikrein is defined as that amount which, when placed in two milliliters of a solution of $5 \times 10^{-4}$ molar benzoyl-L-arginine ethyl ester (BAEE) in PBS pH 8.0 contained in a quartz cuvette having an optical path length of one centimeter and maintained at 37° C., will produce a change in absorbancy of one absorbance unit per minute at a wavelength of 253 nanometers.

To perform the assay for PKA, 0.050 milliliters of the above described solution of PK is warmed to 37° C., and then 0.025 milliliters of the PPF sample is added and the mixture further incubated at 37° C. for an accurately measured time t from about one to about 200 minutes. A 0.025 milliliter sample of the mixture is then withdrawn and immediately added to two milliliters of a solution of $5 \times 10^{-4}$ molar BAEE in PBS pH 8.0, contained in a 1 centimeter quartz cuvette prewarmed at 37° C. The cuvette is then placed in a recording spectrophotometer adjusted to a wavelength of 253 nanometers and the change of absorbancy with time is measured. From the value for the measured rate of change of absorbance $$\left(\frac{\Delta A}{\Delta t}\right)$$

and the known incubation time t, the concentration of PKA in the PPF sample is calculated using the following formula:

$$[PKA] = \frac{3}{t} \ln \frac{0.0167}{0.0167 - \frac{\Delta A}{\Delta t}}$$

where:

t = incubation time in minutes of the PK-PPF mixture $\frac{\Delta A}{\Delta t}$ = measured change in absorbancy with time, in absorbancy units per minute

[PKA] = concentration, in units per milliliter, of PKA in the PPF sample

One unit of PKA is that amount which, in one milliliter, will catalyze the conversion of PK to kallikrein at an initial rate of one unit per minute at pH 7.5, 37° C., when the initial concentration of PK is one unit per milliliter. For convenience, the PKA concentration may be expressed in milli-units per milliliter (mU/ml.), where one milli-unit of PKA is equivalent to 0.001 unit.

EXAMPLE A

A 0.025 milliliter sample of PPF is incubated for 30 minutes at 37° C. with 0.050 milliliter of PK in PBS pH 7.5 having a PK concentration of one unit per milliliter. A 0.025 milliliter aliquot of the mixture is then withdrawn and added to 2.0 milliliters of $5 \times 10^{-4}$ molar BAEE in PBS pH 8.0 and placed in a spectrophotometer adjusted to a wavelength of 253 nanometers and having a cuvette compartment maintained at 37° C. The rate of change of absorbance with time was determined to be 0.0066 absorbancy units per minute.

$$[PKA] = \frac{3}{30} \ln \frac{0.0167}{0.0167 - 0.0066} = 0.0503 \text{ units/milliliter}$$

This PPF solution therefore contains 0.0503 units PKA per milliliter, or 50.3 mU/ml.

EXAMPLE B

When high levels of PKA are suspected, a shorter incubation time should be used.

Another PPF sample was assayed as in Example A except that the incubation time was 5 minutes. The measured rate of change of absorbance was 0.0114 absorbance units per minute.

$$[PKA] = \frac{3}{5} \ln \frac{0.0167}{0.0167 - 0.0114} = 0.689 \text{ units/milliliter}$$

This PPF solution thus contains 689 mU/ml. of PKA.

The Bureau of Biologics requires that the PKA content of PPF be not more than 25 percent of that of a PKA reference standard supplied by the Bureau. When the PKA reference standard is assayed by the above procedure, it is found to contain 65 mU/ml. of PKA. Therefore, to be acceptable, the PKA concentration in PPF solution should be no greater than 25 percent of 65 mU/ml., or about 16 milli-units per milliliter. In the disclosure and claims of this application any statement referring to PPF substantially free of activators of prekallikrein (PKA) is intended to mean solutions of PPF at about a concentration of 5 percent contain no more than about 16 milli-units of PKA per milliliter.

Activation Step in Bradykinin Generation System

The procedure detailed in Example 1 is representative of a preferred method for the bradykinin generating step of the present invention.

EXAMPLE 1

A mixture of 48 liters of Cohn Supernatant II plus III (from Pilot Lot 1) and 48 g. of Super-Cel filter aid was stirred gently for about 14 hours at $-6° \pm 1°$ C. The pH of the mixture is generally about 6.8 and generally rises to as high as about 7.5 during this period.

The mixture was then acidified with a solution prepared by mixing 0.175 liter of 10 molar acetic acid with 4.64 liters of water, cooled to 4° C., and added slowly with stirring to the mixture. The mixture was maintained at about $-8°$ C. and the final pH was $5.30 \pm 0.05$. The mixture was allowed to stand at this temperature for six hours although longer periods, i.e., up to 30 hours, do not appear to have any noticeable effect other than to aid in the precipitation of Cohn Fraction IV-1. Following agitation of the mixture for 2 hours, it was centrifuged using a Sharples S16 continuous flow centrifuge to give a paste of Fraction IV-1 and Super-Cel filter aid weighing 0.822 kg. The Cohn Supernatant IV-1 was then filtered to clarify the solution amounting to 44 liters.

Maintaining this Supernatant IV-1 at about $-8°$ C., 2.68 liters of a solution prepared by diluting 2 liters of 2 M acetic acid to 3 liters with 95 percent ethanol was added slowly with stirring to lower the pH to $4.65 \pm 0.05$. Ethanol (7.95 liters, 95 percent) chilled to $-30°$ C. was added with stirring and the mixture was allowed to stand at about $-8°$ C. for about 10 hours. After stirring for an hour, the mixture was centrifuged (continuous flow) to give 2.8 kg. of a wet paste consisting of about 35 percent of Plasma Protein Fraction, ethanol and water.

EXAMPLE 2

In a procedure similar to that described in Example 1, 46 liters of Supernatant II plus III from Pilot Lot 2 was stirred with 46 g. of Super-Cel filter aid for a period of 15.5 hours and after removal of Fraction IV-1 (1.326 kg.) there was obtained 2.2 kg. of a wet paste of Plasma Protein Fraction.

EXAMPLE 3

By the procedure of Example 1, 47 liters of Supernatant II plus III from Pilot Lot 3 was stirred with 47 g. of Super-Cel filter aid for 16 hours and after removal of Fraction IV-1 (0.691 kg.) there was obtained 2.75 kg. of a wet paste of Plasma Protein Fraction.

EXAMPLE 4

A 300 g. portion of the wet paste from Example 1 was acetone dried by the procedure described in U.S. Pat. No. 2,659,986, incorporated herein by reference, to give 95 g. of dry Plasma Protein Fraction.

EXAMPLE 5

A 300 g. portion of the wet paste from Example 2 was acetone dried to give 109 g. of dry Plasma Protein Fraction.

EXAMPLE 6

A 300 g. portion of the wet paste from Example 3 was acetone dried to give 102 g. of dry Plasma Protein Fraction.

EXAMPLE 7

Twenty separate production lots of about 3000 liters each of Supernatant II plus III were treated with about 3 kg. of Super-Cel filter aid as in Example 1 and, after removing Fraction IV-1, dry powders of Plasma Protein Fraction were obtained as in Example 4.

CONTROL SAMPLES FOR PRODUCTS OF EXAMPLES 4 THROUGH 6

EXAMPLE 8

The procedures of Examples 1 and 4 were applied to Supernatant II plus III from Pilot Lot 1 with the exception that no Super-Cel filter aid was used.

EXAMPLE 9

The procedures of Examples 1 and 4 were applied to Supernatant II plus III from Pilot Lot 2 with the exception that no Super-Cel filter aid was used.

EXAMPLE 10

The procedure of Examples 1 and 4 were applied to Supernatant II plus III from Pilot Lot 3 with the exception that no Super-Cel filter aid was used.

DESTRUCTION OF BRADYKININ

EXAMPLE 11

The dry Plasma Protein Fraction of Example 4 was dissolved at 5° C. in a solution of salts such that the constitution of the final solution was approximately 5 percent protein and contained 0.25 percent sodium acetate trihydrate, 0.24 percent sodium chloride, 0.105 percent acetyl-DL-tryptophan and 0.066 percent sodium caprylate. The pH of the solution was $7.0 \pm 0.05$. After filtering to clarify the solution, aliquots were held at $+5°$ and $+37°$ C. for 2, 6 and 24 hours, then each aliquot was subsequently heated for 12 hours at 60° C. and then assayed for bradykinin. Results are presented in Table 1.

EXAMPLE 12

The procedure described in Example 11 was applied to the product of Example 5.

EXAMPLE 13

The procedure described in Example 11 was applied to the product of Example 6.

CONTROL SAMPLES FOR PRODUCTS OF EXAMPLES 11 THROUGH 13

EXAMPLE 14

The procedure of Example 11 was applied to the product of Example 8.

EXAMPLE 15

The procedure of Example 11 was applied to the product of Example 9.

EXAMPLE 16

The procedure of Example 11 was applied to the product of Example 10.

Bradykinin and kininogen levels were determined on aliquots of solutions of each of Examples 11–16 heated at 60° C. for 12 hours immediately after their preparation (0 hold time) to serve as controls. See Table 1.

TABLE 1

Bradykinin (BK) and Kininogen Levels of Heat-Stable Plasma Protein Fraction (PPF) Bradykinin Content (ng/ml) of 5% PPF Solutions

| Example | Hold Time - 0 Hours | | | Hold Time at +5° C. | | | Hold Time at +37° C. | | |
|---|---|---|---|---|---|---|---|---|---|
| | BK | Kininogen-BK Equivalent | Total Potential BK | 2 hrs | 6 hrs | 24 hrs | 2 hrs | 6 hrs | 24 hrs |
| 11 | 36 | 0 | 36 | 3.4 | 1.5 | <1 | <1 | <1 | <1 |
| 14 | 35 | 180 | 215 | 84 | 52 | 9 | 55 | 38 | 38 |
| 12 | 36 | 0 | 36 | 5.0 | 3.0 | 1.0 | 2.0 | <1 | <1 |
| 15 | 31 | 222 | 253 | 70 | 46 | 13 | 60 | 40 | 32 |
| 13 | 62 | 0 | 62 | 2.8 | 1.5 | <1 | <1 | <1 | <1 |
| 16 | 39 | 246 | 285 | 238 | 245 | 290 | 70 | 92 | 120 |

The results in Table 1 show the effectiveness of the process of this invention in removing kininogen and bradykinin from Plasma Protein Fraction. Morichi and Izaka (Transfusion 16, pp. 178–181, 1976) have shown that an unheated solution of Plasma Protein Fraction obtained from Supernatant IV-1, when treated with human urinary kallikrein, results in the release of a kinin-like substance. They also observed the subsequent rapid inactivation of this kinin and suggested a kininase was present since they showed that when synthetic bradykinin was added to this solution, the bradykinin was entirely degraded. I have observed that some production lots of an unheated solution of Plasma Protein Fraction prepared as disclosed in U.S. Pat. No. 2,958,628, when held for at least a day to allow for the bradykinin-degrading effect of kininase, showed the presence of only a few nanograms/ml. of bradykinin. However, in contrast to these observations and to what Morichi et al have indicated, I have observed that despite the holding of similar production lots, bradykinin still remains present at fairly high levels (see Examples 14 and 15 in Table 1). In fact, in the production lot of Example 16, bradykinin increased on standing to very high levels. It is apparent from the data on Examples 11–13 with the treatment of solutions containing PPF with a siliceous substance such as Super-Cel is essential if one wants to be assured of obtaining a product substantially free of bradykinin as well as kininogen.

EXAMPLE 17

Twenty-two production lots of 1000 liters each of 5 percent protein solution were prepared according to the procedure described in Example 11, using the dry powders of Example 7. These solutions were first clarified, held at 5° C. for 24 hours, then sterile filtered into sterile glass vials and heated at 60° C. for 10 hours. Bradykinin was determined on representative samples. In all lots, the level of bradykinin was below the level of detection (less than 1 nanogram per milliliter). When assayed for levels of kininogen, the bradykinin equivalents averaged about 5 nanograms per milliliter and was in no case greater than 9 ng./ml. In contrast, production lots of 5 percent solutions of PPF prepared by the usual Hink process which does not incorporate the process of this invention, sometimes contain as much as 150 ng./ml. of bradykinin and kininogen equivalent to as much as 300 ng./ml. of bradykinin.

Diafiltration as an Alternative Procedure For Simultaneous Destruction and Removal of Bradykinin

EXAMPLE 18

Approximately a 5.7 percent solution of Plasma Protein Fraction was prepared by dissolving 1.1 kg. of the wet paste of Example 1 in 5.5 liters of water. The pH was adjusted to about neutrality with sodium carbonate and the solution was diafiltered at 3° C. using an Amicon DC-30 diafiltration unit with two SM-10 cartridges (Amicon Corp., Lexington, Mass.). Diafiltration was continued until a total of about 31 liters of dialyzate had been collected, requiring about 5 hours. To the retentate (5.8 liters) was added a solution of 4 g. sodium caprylate, 5.92 g. acetyl-DL-tryptophan, 3.99 g. sodium carbonate monohydrate, 17.6 g. sodium chloride and 23.2 g. sodium acetate trihydrate in 315 ml. water. The pH was adjusted to 6.9 by the addition of a small amount of sodium carbonate. After sterile filtering the solution, it was heated 10 hours at 60° C. The solution assayed 1 ng./ml. of bradykinin. It contained no kininogen since the 5 percent solution prepared from the acetone dried powder derived from the wet paste of Example 1 was shown to be free of kininogen (See Example 11 in Table 1).

EXAMPLE 19

By the same procedure described in Example 18 but using 0.73 kg. of the wet paste of Example 2, a solution of Plasma Protein Fraction was obtained whose level of bradykinin was less than 1 ng./ml.

EXAMPLE 20

By the procedure of Example 18 but using 1.65 kg. of the wet paste of Example 3, a solution of Plasma Protein Fraction was obtained which assayed 1 ng./ml. of bradykinin.

ULTRAFILTRATION-DIAFILTRATION AS AN ALTERNATIVE PROCEDURE FOR ELIMINATING BRADYKININ

EXAMPLE 21

Following the procedure of Example 1, approximately 100 liters of Cohn Supernatant II plus III was treated with Super-Cel filter aid and Cohn Fraction IV-1 was removed therefrom. About 75 liters of the Supernatant IV-1 was adjusted to neutrality with sodium carbonate and ultrafiltered through a Romicon ultrafiltration unit HF-22-20 PM-10 (Romicon Corp., Woburn, Mass.) at 0° to 10° C. After the Supernatant IV-1 (original protein concentration of 2.31 percent) had been concentrated to about 12 percent protein, it was then diafiltered with water using five changes of volume. The total ultrafiltration-diafiltration procedure required about 24 hours. The resulting solution of Plasma Protein Fraction contained essentially no ethanol or salts and its levels of bradykinin and kininogen were below detectable levels.

DESTRUCTION OF PREKALLIKREIN ACTIVATORS (PKA)

A. DESTRUCTION OF PKA FOLLOWING PASTEURIZATION TO DESTROY HEPATITIS VIRUS

EXAMPLE 22

Whereas all of the production lots as described in Example 17 were found to contain less than 1 ng./ml. of bradykinin, essentially all lots had levels of PKA substantially in excess of the acceptable level of about 16 mU/ml. A typical lot was found to contain 76 mU/ml. Aliquots of this lot were heated at 60° C. at pH 5.5, 6.0, and 7.0 for various periods of time. The PKA levels were then determined.

TABLE 2

| | PKA Destruction in Solutions of PPF (5%) At Various pH | | | |
|---|---|---|---|---|
| | PKA Value, mU/ml. | | | |
| pH | 0.5 hr. | 2 hr. | 6 hr. | 24 hr. |
| 5.5 | 26.6 | 19 | 7.6 | 2.3 |
| 6.0 | 57 | 49.5 | 38 | 19 |
| 7.0 | 64.6 | 60.8 | 57 | 30.4 |

At an initial PKA value of 76 mU/ml., destruction of the PKA to an acceptable level can be accomplished between 2 and 6 hours at pH 5.5 and a little more than 24 hours at pH 6.0. Following the adjustment of the pH to about neutrality, these solutions are suitable for injection.

EXAMPLE 23

Aliquots of another lot from Example 17, which contained 100 mU/ml. of PKA, were heated at various temperatures at pH 7.0 and the PKA values were determined at various intervals of time. The half-life of PKA was found to be essentially uniform at any one temperature.

TABLE 3

| Destruction of PKA at Various Temperatures | |
|---|---|
| Temp., °C. | 50% Loss of PKA in Hours |
| 56 | 55 |
| 60 | 14.7 |
| 62 | 8.5 |
| 65 | 0.6 |

From Table 3, it can be seen that, for example at 65° C., it requires about 1.8 hours to reduce the level of PKA from 100 mU/ml. to about 12 mU/ml. At 56° C., it requires about 5 to 6 days to lower the PKA to acceptable levels. Other lots which had either somewhat more or less PKA were heated in a similar fashion and the half-lifes of PKA were substantially the same at these temperatures.

B. DESTRUCTION OF PKA PRIOR TO PASTEURIZATION

EXAMPLE 24

The product of Example 4 was reconstituted with a solution of stabilizers and buffer as described in Example 11, was sterile filtered, and was immediately assayed for PKA and found to contain 550 mU/ml. An aliquot of this solution was held at room temperature and samples taken at 3 and 24 hours for PKA determinations.

TABLE 4

| PKA Destruction at Room Temperature | |
|---|---|
| Time, hrs. | PKA, mU/ml. |
| 3 | 250 |
| 24 | 6 |

This example illustrates a preferred final step in a method for obtaining a solution of Plasma Protein Fraction since not only is heating not required but also substantially complete kininogen and bradykinin destruction has been effected in this period of time at this temperature. The solution is then pasteurized at 60° C. for 10 hours and is suitable for injection.

EXAMPLE 25

An aliquot of the same reconstituted solution which was used in Example 24 was kept at 4° C. and a sample taken at 24 hours contained 100 mU/ml. of PKA.

This solution was sterile filtered and portions were then heated at 60° C. at pH values ranging from 5.5 to 8.2 and samples taken at 0.5, 2 and 4 hour intervals for PKA analysis.

TABLE 5

| PKA Destruction at Various pH at 60° C. | | | |
|---|---|---|---|
| | PKA mU/ml., at | | |
| pH | 0.5 hr. | 2 hr. | 4 hr. |
| 8.2 | 39.5 | 16.1 | 9.2 |
| 7.5 | 57.4 | 36.0 | — |
| 6.9 | 60.8 | 37.4 | 30.4 |
| 6.5 | 43.8 | 23.7 | 16.5 |
| 6.0 | 17.5 | 6.0 | 3.7 |
| 5.5 | 5.9 | 1.2 | 0.6 |

This is representative of another preferred method for obtaining a solution of PPF substantially free of PKA and bradykinin since kininogen and bradykinin are also destroyed at this lower temperature in this interval of time. Following pH adjustments to about neturality where necessary, the solutions are then heated for 10 hours at 60° C. and those which had PKA values of around 36 mU/ml. or lower would be suitable for injection since the 10 hours at 60° C. would have essentially reduced the PKA by a factor of 2.

EXAMPLE 26

The procedure described in column 3 and Example 1 of U.S. Pat. No. 4,017,470 (Izaka et al) was conducted on Fraction IV-1 paste to determine whether the final product was substantially free of bradykinin, kininogen and activators of prekallikrein.

A mixture of 100 g. of Fraction IV-1 paste (containing about 40% protein) in distilled water was adjusted to pH 7.2 and the resulting mixture made up to a volume of 600 ml. with water. This mixture was analyzed for PKA and no measureable amount could be detected. As a departure from the Izaka et al procedure, the mixture was then stirred with 5 g. of Super-Cel filter aid at about 5° C. overnight. PKA could still not be detected which suggested this protein fraction probably contains little or no Hageman factor. The filter aid was removed and a concentrated sample of PKA was added to the mixture in an amount that the mixture now contained 40 milli-units per milliliter. To the mixture was then added butyric acid to a final concentration of 5% and the solution was heated for 2 hours at 58° C. The mixture was filtered and the filtrate now contained no detectable amount of PKA. To the solution was added 0.5 g. of Rivanol, the mixture was stirred several hours and then centrifuged. The solution was mixed with ammonium sulfate to a concentration of 75%. The precipitated protein was collected by centrifugation and redissolved in a small amount of water and dialyzed against water. The dialyzed solution was then stirred with silica gel (3 W/V%) overnight and then filtered. The final solution contained 5.8% protein, and contained no detectable amounts of bradykinin or PKA. However, considerable kininogen was present, there being 45 nanograms bradykinin equivalent per milliliter. This experiment clearly shows the process of Izaka et al does not provide a protein fraction derived from Fraction IV-1 which is substantially free of kininogen.

From the foregoing description, one skilled in the art can make various changes and modifications of the procedures without departing from the spirit and scope thereof.

I claim:

1. A sterile aqueous solution of heat-stable Plasma Protein Fraction (Human) suitable for injection, wherein about 5 grams of Plasma Protein Fraction (Human) per 100 milliliters of sterile aqueous solution contains no greater than about 16 milli-units per milliliter Factor XIIa and fragments thereof capable of activating prekallikrein, no greater than about 10 nanograms bradykinin equivalents per milliliter of kininogen, and less than about 10 nanograms per milliliter of bradykinin, said Plasma Protein Fraction (Human) being a mixture of constituent plasma protein isolated from human plasma by a modified Cohn fractionation process and containing at least 83% albumin and no more than 17% alpha and beta globulins having molecular weights similar to that of albumin and no more than 1% gamma globulin.

2. The solution of claim 1 wherein the protein concentration is about 5 percent.

3. The solution of claim 1 which includes a stabilizer selected from the group consisting of sodium acetyltryptophan and sodium caprylate.

* * * * *